United States Patent
Baumann

[19]

[11] Patent Number: 6,059,739
[45] Date of Patent: May 9, 2000

[54] METHOD AND APPARATUS FOR DEFLECTING A CATHETER OR LEAD

[75] Inventor: James C. Baumann, Buffalo, Minn.

[73] Assignee: Medtronic, Inc., Minneapolis, Minn.

[21] Appl. No.: 09/087,482

[22] Filed: May 29, 1998

[51] Int. Cl.$^7$ .................................................. A61M 25/01
[52] U.S. Cl. ............................................. 600/585; 604/95
[58] Field of Search ..................................... 607/116, 119, 607/122; 604/95, 280, 282; 606/129; 600/585, 433, 434

[56] References Cited

U.S. PATENT DOCUMENTS

| | | |
|---|---|---|
| 4,033,357 | 7/1977 | Helland et al. . |
| 4,136,703 | 1/1979 | Wittkampf . |
| 4,488,561 | 12/1984 | Doring . |
| 4,506,680 | 3/1985 | Stokes . |
| 4,572,605 | 2/1986 | Hess . |
| 4,676,249 | 6/1987 | Arenas . |
| 4,727,877 | 3/1988 | Kallok . |
| 4,815,478 | 3/1989 | Buchbinder et al. . |
| 4,898,577 | 2/1990 | Badger et al. ............................ 604/95 |
| 4,922,607 | 5/1990 | Doan et al. . |
| 4,940,062 | 7/1990 | Hampton et al. . |
| 5,040,543 | 8/1991 | Badera et al. . |
| 5,115,818 | 5/1992 | Holleman et al. . |
| 5,170,787 | 12/1992 | Lindegren . |
| 5,282,844 | 2/1994 | Stokes et al. . |
| 5,327,906 | 7/1994 | Fideler . |
| 5,473,812 | 12/1995 | Morris et al. . |
| 5,662,119 | 9/1997 | Brennen et al. . |
| 5,728,148 | 3/1998 | Bostrom et al. . |
| 5,728,149 | 3/1998 | Laske et al. . |

*Primary Examiner*—William E. Kamm
*Assistant Examiner*—George R. Evanisko
*Attorney, Agent, or Firm*—Reed A. Duthler; Harold R. Patton

[57] ABSTRACT

An apparatus for deflecting a catheter or lead, for example a deflectable stylet or guidewire. The device includes an outer tubular member, a tension member mounted within the outer tubular member and coupled to the outer member and a handle mounted at the proximal end of the tubular member. The handle includes a major handle portion which has a rotatable knob located at its distal end, surrounding a proximal portion of the outer tubular member and provided with inwardly directed threading and an inner slider member provided with outwardly directed threading engaging the inwardly directed threading of the knob. The slider is advanced or retracted longitudinally within the handle by rotation of the knob but is rotationally fixed with regard to the major handle portion. The outer tubular member is engaged at its proximal end with the inner slider member and the tension wire is fixedly engaged with the major handle portion, whereby rotation of the knob results in advancement or retraction of the outer tubular member relative to the tension wire and the major portion of the handle, which in turn causes the deflection of the outer tubular member.

2 Claims, 3 Drawing Sheets

METHOD AND APPARATUS FOR DEFLECTING A CATHETER OR LEAD

BACKGROUND OF THE INVENTION

The present invention relates generally to implantable leads and catheters and more particularly to mechanisms for deflecting implantable leads and catheters to assist in guiding them through the vascular system.

Over the years, quite a number of mechanisms have been disclosed and employed to deflect catheters and implantable leads. These have taken the form of deflectable guidewires and deflectable stylets, typically operable from the proximal end of the lead or catheter, which controllably impart a curve to the distal portion of the catheter. One group of devices comprise deflectable stylets or guidewires which employ a straight, tubular outer member with a curved inner member, the inner and outer members movable relative to one another. Examples of this type of deflection mechanism are disclosed in U.S. Pat. No. 4,136,703 issued to Wittkampf and U.S. Pat. No. 5,728,148 issued to Bostrom et al. Alternatively, deflection devices employing a curved outer member and a relatively straight inner member are also known to the art, as disclosed in U.S. Pat. No. 4,676,249 issued to Arenas and U.S.

U.S. Pat. No. 5,040,543 issued to Badera et al. In devices of both types, the relative position of the inner member with respect to the outer member determines the degree to which the curved member (inner or outer) is allowed to display its preset curvature.

A more commonly employed approach to providing controllable deflection employs a generally straight outer member and a tension or push wire located within the outer member which on advancement or retraction causes the outer member to bend. Examples of such deflection mechanisms can be found in U.S. Pat. No. 4,815,478 issued to Buchbinder et al., and U.S. Pat. No. 4,940,062 issued to Hampton et al.

Particularly in the context of deflectable stylets intended for use in conjunction with implantable medical leads such as pacing and cardioversion leads, steerable stylets employing this third type of deflection mechanism are disclosed in U.S. Pat. No. 5,662,119 issued to Brennan et al., U.S. Pat. No. 5,170,787 issued to Lindegren, and U.S. Pat. No. 5,327,906 issued to Fideler et al, all of which are incorporated herein by reference in their entireties.

While all of the mechanisms disclosed in the above cited prior art patents are at least to some degree workable, there is still a perceived need for a deflectable stylet or guidewire which is simple to manufacture and easy to use.

BACKGROUND OF THE INVENTION

The present invention is directed toward providing a deflectable stylet or guidewire which is both simple to manufacture and readily operable using only one hand. The present invention accomplishes these goals by means of a deflection mechanism which employs a minimum of moving parts, and which is arranged to facilitate easy control of the degree of curvature displayed by the stylet or guidewire. More particularly, the present invention comprises a deflectable stylet or guidewire which is provided with a handle which has located at its distal end a rotatable and slidable knob or spinner surrounding the deflectable stylet or guidewire, provided with inwardly directed threading in conjunction with an inner slider member provided with outwardly directed threading, which may be advanced or retracted longitudinally within the handle by rotation of the knob or spinner but which is rotationally fixed with regard to the remainder of the handle assembly. An additional benefit of the inventive design is that the knob and the inner slider member together may be slid distally relative to the handle, providing a mechanism for more quickly forming a curve at in the stylet or guidewire. This feature is particularly beneficial when a curve is needed only temporarily, for example in conjunction with deflecting the tip of the stylet to facilitate entry into a desired blood vessel, such as the coronary sinus.

The steerable stylet or guidewire is provided with an outer tubular member and an inner tension wire, with the outer tubular member engaged at its proximal end with the inner slider member of the handle and the tension wire of the deflectable stylet or guidewire fixedly engaged with the remainder of the handle assembly. By means of this configuration, rotation of the knob or spinner produces advancement or retraction of the outer, tubular member of the deflectable stylet or guidewire relative to the handle assembly, which in turn causes the deflected stylet or guidewire to exhibit a desired degree of curvature. Simply sliding the knob or spinner and the inner slider member distally together also serves to move the outer tubular member of the stylet relative to the tension wire, inducing a desired degree of cuvature.

By means of the mechanism described above, a deflectable stylet is provided which conveniently allows for placement of the spinner or knob at the distal end of the handle where it may be readily grasped by the thumb and forefinger of the user, while the remainder of the handle may be grasped by the palm and the other three fingers of the user's hand. The design of the present invention requires only two moving parts within the handle assembly in order to provide for deflection of the distal tip of the guidewire or catheter, providing an assembly which is relatively inexpensive and simple to manufacture.

The distal portion of the handle is provided with a recess which allows for insertion of the connector assembly of an implantable electrical lead such as a pacemaker or defibrillator lead, allowing the connector assembly to be located in a fixed relationship with the inner, moveable slider member of the handle, while allowing the knob or spinner member to freely rotate around the connector assembly of the lead. The recess also inherently serves as a strain relief, preventing bending or kinking of the deflectable guidewire at the point it exits the slider.

DETAILED DESCRIPTION OF THE PREFERRED EMBODIMENTS

Figure 1:
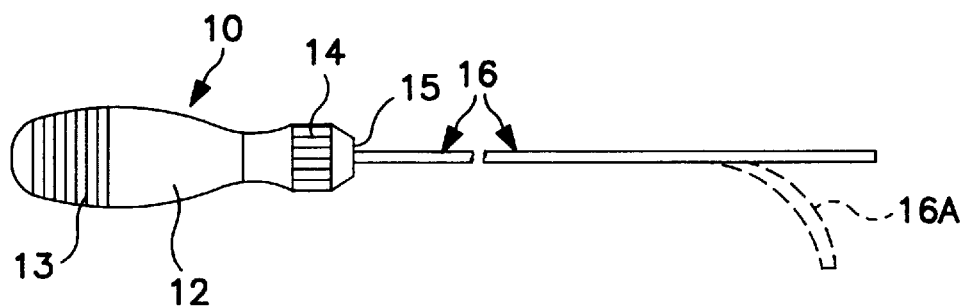
FIG. 1 is a plan view of a deflectable stylet according to the present invention.

FIG. 1 illustrates a plan view of a deflectable stylet according to the present invention. The deflectable stylet 16 is provided with a handle 10 provided with a main handle portion 12 and a spinner or knob portion 14, mounted rotatably with respect to the primary handle portion 12. The primary handle portion 12 is provided with circumferential grooving at its proximal end, while the spinner or knob 14 is may be provided with external ribbing or knurling as illustrated. The deflectable stylet 16 exits from a proximal recess 15, within spinner or knob 14. The rotation of spinner or knob 14 or distal advancement of knob 14 relative to the handle 12 causes deflection of the distal portion of stylet 16 to a curved configuration as illustrated at 16A.

Deflectable stylet 16 may take the form of any known deflectable stylet employing an outer tubular member and an inner tension wire which, when it applies tension to the distal tip of deflectable stylet 16, causes the tip of the stylet to curve. Appropriate designs for the deflectable stylet 16 include those described in the Brennen et al, Lindegren and Fideler patents discussed above and incorporated herein by reference in their entireties. Alternatively, deflectable stylet 16 may be replaced by a deflectable guidewire, for example, as disclosed in the above-cited Buchbinder patent, also incorporated herein by reference in its entirety. In all of these various guidewires and stylets, the basic structure of the deflectable stylet or guidewire consists of an outer tube which in a relaxed condition displays a generally straight configuration, and an internal tension wire coupled to the distal portion of the guidewire, and arranged such that upon application of tension to the distal tip of the guidewire or stylet, the distal portion of the guidewire or stylet exhibits a curved configuration.

Figure 2:
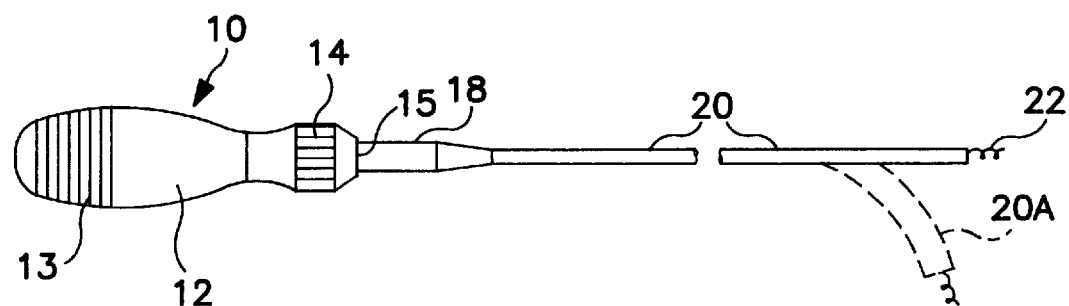
FIG. 2 is a plan view of the deflectable stylet of FIG. 1 shown inserted into an implantable cardiac pacing lead.

FIG. 2 is a plan view of the deflectable stylet of FIG. 1 inserted into a cardiac pacing lead 20. Cardiac pacing lead 20 is provided with a connector assembly 18 located at its proximal end, which typically carries a connector pin as is typical of cardiac pacing leads. For example, the distal portion of the connector assembly 18 may correspond to the IS-1 connector standard as disclosed in U.S. Pat. No. 4,922,607 issued to Doan et al., also incorporated herein by reference in its entirety. However, other connector configurations, such as disclosed in U.S. Pat. No. 4,488,561 issued to Doring or U.S. Pat. No. 4,572,605 issued to Hess et al., both also incorporated herein by reference in their entireties, may also be employed. At the distal end of pacing lead 20 is located a fixed helical electrode 22, such as that disclosed in U.S. Pat. No. 5,473,812 issued to Morris et al. and incorporated herein by reference in its entirety, which is screwed into heart tissue in order to stimulate the heart. However, any other type of known pacing electrode may be substituted for electrode 22, or alternatively other types of electrodes such as cardioversion or defibrillation electrodes may be added to or substituted for electrode 22. Examples of pacing and cardioversion electrodes generally that might be employed in conjunction with a lead to be deflected by the deflectable stylet of the present invention include those described in U.S. Pat. No. 5,282,844 issued to Stokes et al., U.S. Pat. No. 4,506,680 issued to Stokes, U.S. Pat. No. 4,033,357 issued to Helland et al., U.S. Pat. No. 4,727,877 issued to Kallok, U.S. Pat. No. 5,115,818 issued to Holleman et al. and U.S. Pat. No. 5,728,149 issued to Laske et al., all also incorporated herein by reference in their entireties.

As illustrated, the connector assembly 18 of the lead 20 is inserted into the distal facing opening 15 within spinner or knob 14. The spinner or knob 14 is free to rotate and slide with respect to connector assembly 18. The internal slider member (not visible in this view) located within handle 10 may either frictionally engage the connector pin of the connector assembly 18, or may be free to rotate with respect to the connector pin. For example, in the context of a device employing a fixed helical electrode, rotation of the entire lead with respect to the deflectable stylet would be required in order to screw the helical electrode 22 into heart tissue. However, in the context of a lead employing a tined electrode or employing other electrodes not requiring rotation of the lead body to accomplish fixation, the inner slider member of the handle 10 might frictionally engage the connector pin of connector assembly 18, further facilitating the steering of the lead through the vascular system to the desired location within the heart.

Figure 3:
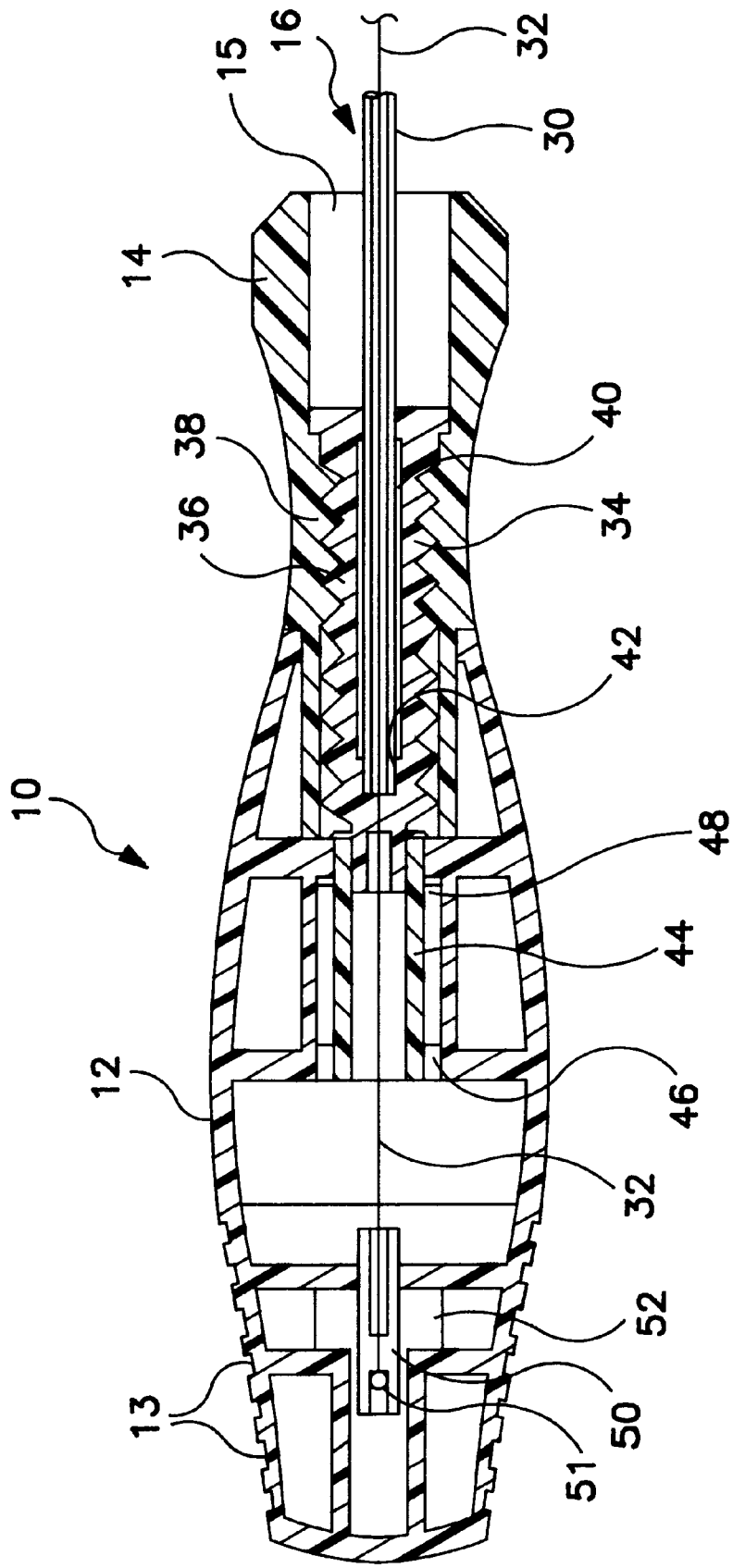
FIG. 3 is a sectional view through the handle portion of the deflectable stylet illustrated in FIG. 1.

FIG. 3 illustrates a sectional view through the handle 10 of the deflectable stylet illustrated in FIG. 1. The handle comprises a main handle portion 12 and a spinner or knob portion 14, both of which may be molded plastic parts. Spinner 14 is provided with inwardly facing screw threads 38 which engage with correspondingly outwardly facing screw threads 36 on the inner slider member 34. Fixedly coupled to the proximal end of slider 34 is a cylindrical extension 44 which is provided with two oppositely arranged outwardly projecting tabs 46 which engage with corresponding longitudinal grooves 48 formed in the major handle portion 12. Slider 34 and extension 44 may also be molded plastic parts. Interaction of the outwardly extending tabs 46 and the grooves 48 prevent rotation of tubular extension 44 and of slider member 34 relative to the major handle portion 12. As such, rotation of knob or spinner 14 relative to the major handle portion 12 causes proximal or distal movement of slider member 34 and extension 44 relative to both the major handle portion 12 and the knob or spinner 14.

The deflectable stylet 16 is arranged such that the outer tubular member 30, which be formed of stainless steel or nitinol tubing is fixedly mounted within the proximal portion 42 of the inner lumen 40 of slider 34, while the tension wire 32 extends through slider 34 to an anchoring mechanism which comprises a threaded rod 50 and an associated adjuster nut 52, located within the major handle portion 12. The threaded rod 50 is provided with a lumen through which tension wire 36 passes, and is arranged such that a ball 51 or other expanded diameter portion located at the proximal end of tension wire 32 anchors the wire with respect to threaded rod 50. Threaded rod 50 and nut 52 are both mounted rotationally fixed with respect to major handle portion 12, with adjuster nut 50 employed to position tension wire 32 so that in the circumstance in which the internal slider 34 is located at its most proximal position (as illustrated), no tension is applied to the distal tip of the outer tubular member 30 of the deflectable stylet 16, so that the deflectable stylet 16 displays a straight configuration. On rotation of spinner or knob 14 to advance inner slider member 34 with respect to the major handle portion 12, the outer tubular portion 30 of the deflectable stylet is also advanced with respect to tension wire 32, causing tension wire 32 to apply tension to the distal tip of the tubular member 30, correspondingly causing deflection of the tubular member.

Opening 15 in the distal portion of the knob or spinner 14 is sized to accept the connector assembly of the lead with which the deflectable stylet is intended to be used, with sufficient clearance, so that rotation of knob or spinner 14 does not cause corresponding rotation of the connector assembly. The internal lumen 40 of the inner slider member 34 may be sized either to frictionally engage a connector pin at the proximal end of the lead connector assembly, or may be sized to be slightly greater than the connector pin of the associated lead. If the opening 40 is sized to be somewhat greater than the outer diameter of the connector pin, then the entire lead may be rotated with respect to the deflectable stylet. This is particularly desirable in the context of a lead as illustrated in FIG. 1 which employs a fixation helix 22 (FIG. 2), fixedly mounted to the distal end of the lead body, as it allows the lead to be screwed into the tissue, around the stylet, in its deflected configuration. As noted above, however, as noted in the case of a lead employing a tined electrode or other fixation mechanism, it may be desirable to size the internal lumen 40 so that it frictionally engages a connector pin on the lead.

Figure 4:
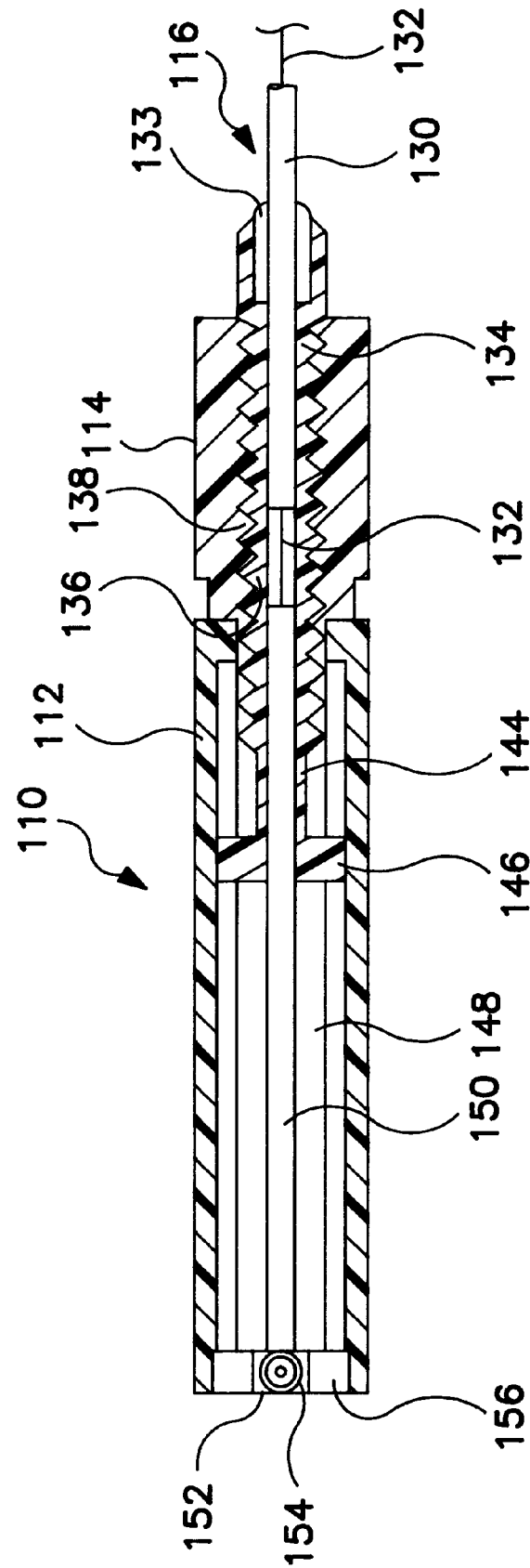
FIG. 4 is a sectional view through an alternative embodiment of the handle portion of a deflectable stylet according to the present invention.

FIG. 4 illustrates a cross-sectional view through an alternative embodiment of the handle portion of a deflectable stylet according to the present invention. The deflectable stylet 116 corresponds to deflectable stylet 16 illustrated in FIGS. 1 and 3 above, and includes an outer tubular member 130 which may take the form of a metal tube and an inner tension wire 132. Like the handle illustrated in FIG. 3, the handle 110 illustrated in FIG. 4 includes a spinner or knob portion 114 which is rotatably and slidably mounted relative to a major handle portion 112, which serves to advance or retract an inner slider portion 134, which is mechanically coupled to the outer tube 130 of deflectable stylet 116.

The proximal portion of the internal slider member 134 is provided with outwardly facing projections 146 which engage with a correspondingly shaped inner surface 148 of the major handle member 112 to prevent rotation of inner slider member 134 relative to handle 112. The proximal end of tension wire 132 is crimped, welded or otherwise coupled to a proximal tubular member 150 which may also be fabricated of hypo tubing and which is provided with a loop 154 at its proximal end. Tubular member 150 extends through the internal lumen through slider member 134, but is sized so that slider member 134 may be freely be moved proximally or distally with respect to the tubular member 150. Tubular member 150 is maintained in fixed longitudinal relationship with the major handle portion 112 by means of a pin 154 which passes through loop 152 and is anchored in end piece 156 of the handle 110. Located at the proximal end of the assembly is strain relief 133, which prevents undue stress at the point at which deflectable stylet 116 exits inner slider member 134. Operation of the device illustrated in FIG. 4 corresponds to that of the device illustrated in FIG. 3, with rotation or sliding of the knob or spinner 14 relative to the major handle portion 112 causing advancement of the outer tubular member 130 of deflectable stylet 116, correspondingly causing tension wire 132 to exert tension on the distal end of the outer tubular member 130 and causing it to assume a desired curved configuration.

While the above illustrated embodiments take the form of deflectable stylets, it should be understood that the present invention is equally applicable to deflectable guidewires as discussed above. Moreover, while it is believed that the most likely commercial embodiment of the present invention is a guidewire or stylet which is removably insertable into a catheter or lead body, the present invention may also have utility in the context of a deflection mechanism which is fabricated as a permanent part of a deflectable catheter, such as an electrophysiology mapping or ablation catheter, or other catheters of the type which typically include deflection mechanisms and handles permanently affixed to the catheters or lead bodies. As such, the above disclosed embodiments should be considered exemplary rather than limiting with regard to the scope of the claims that follow.

In conjunction with the above specification, I claim:

1. Apparatus for deflecting one of a catheter or lead, comprising:

an outer tubular member;

a tension member mounted within the outer tubular member and coupled to the outer member;

a handle comprising a major handle portion, a distal end of the major handle portion having a rotatable knob, the knob surrounding a proximal portion of the outer tubular member and provided with inwardly directed threading; and an inner slider member provided with outwardly directed threading engaging the inwardly directed threading of the knob, wherein the slider is advanced or retracted longitudinally within the handle by rotation of the knob but is rotationally fixed with regard to the major handle portion; wherein a proximal end of the outer tubular member is engaged with the inner slider wire and the tension wire is fixedly engaged with the major handle portion, whereby rotation of the knob results in advancement or retraction of the outer tubular wire relative to the tension wire and the major portion of the handle, which in turn causes the deflection of the outer tubular member.

2. Apparatus for deflecting one of a catheter or lead, comprising:

an outer tubular member;

a tension member mounted within the outer tubular member and coupled to the outer member;

a handle comprising a major handle portion, a distal end of the major handle portion having a rotatable and longitudinally slidable knob, the knob surrounding a proximal portion of the outer tubular member and provided with inwardly directed threading; and an inner slider member provided with outwardly directed threading engaging the inwardly directed threading of the knob, wherein the slider is advanced or retracted longitudinally within the handle by rotation of the knob but is rotationally fixed with regard to the major handle portion; wherein a proximal end of the outer tubular member is engaged with the inner slider wire and the tension wire is fixedly engaged with the major handle portion, whereby rotation or sliding of the knob results in advancement of the outer tubular wire relative to the tension wire and the major portion of the handle, which in turn causes the deflection of the outer tubular member.

* * * * *